United States Patent [19]

Wilk

[11] Patent Number: 5,209,721

[45] Date of Patent: May 11, 1993

[54] LAPAROSCOPIC SURGICAL DEVICE AND RELATED METHOD

[76] Inventor: Peter J. Wilk, 185 W. End Ave., New York, N.Y. 10023

[21] Appl. No.: 830,117

[22] Filed: Jan. 31, 1992

[51] Int. Cl.$^5$ .................................. A61M 37/00
[52] U.S. Cl. ........................ 604/26; 128/24 AA; 128/898; 128/747
[58] Field of Search .......... 604/22, 26, 49, 164; 128/747, 748, DIG. 12, DIG. 13, 24 AA, 898

[56] References Cited

U.S. PATENT DOCUMENTS

| | | | |
|---|---|---|---|
| 3,556,079 | 4/1968 | Omizo | 128/24 AA |
| 4,068,659 | 1/1978 | Moorehead | 128/214.4 |
| 4,207,887 | 6/1980 | Hiltebrandt et al. | 604/26 |
| 4,356,826 | 11/1982 | Kubota | 128/748 |
| 4,431,006 | 2/1984 | Trimmer et al. | 128/24 AA |
| 4,464,169 | 8/1984 | Semm | 604/26 |
| 4,676,774 | 6/1987 | Semm et al. | 604/26 |
| 4,869,717 | 9/1989 | Adair | 604/26 |
| 4,874,362 | 10/1989 | Wiest et al. | 604/26 |
| 4,966,578 | 10/1990 | Baier et al. | 604/26 |
| 5,002,557 | 3/1991 | Hasson | 604/26 |
| 5,006,109 | 4/1991 | Douglas et al. | 604/26 |
| 5,013,294 | 5/1991 | Baier | 604/26 |
| 5,098,375 | 3/1992 | Baier | 604/26 |
| 5,131,394 | 7/1991 | Gelbach | 128/662.05 |
| 5,131,395 | 7/1992 | Gelbach | 128/662.05 |

FOREIGN PATENT DOCUMENTS

| | | |
|---|---|---|
| 0190719 | 8/1986 | European Pat. Off. |
| 0423855A1 | 4/1991 | European Pat. Off. |
| 2148674 | 4/1973 | Fed. Rep. of Germany |

OTHER PUBLICATIONS

Promotional brochure of MeadoxSurgimed for Surgical Doppler, copyright date 1991, Meadox Surgimed.
Promotional brochure for INTRADOP ™ Intraoperative Doppler, distributed by Nova Endoscopy.

Primary Examiner—Stephen C. Pellegrino
Assistant Examiner—Michael Rafa
Attorney, Agent, or Firm—R. Neil Sudol; Henry D. Coleman

[57] ABSTRACT

A device for use in laparoscopic surgical operations comprises a Veress needle assembly including a Veress needle, and a pressure sensor or an ultrasound sensor operatively connected to the needle assembly for monitoring pressure. In using the device to insufflate or pressurize a patient's abdomen with carbon dioxide, the needle is connected to a pressure source upon the detection of a drop in pressure or in response to an ultrasonic image or other indication as to the locations of internal organs and tissues of the patient.

7 Claims, 1 Drawing Sheet

LAPAROSCOPIC SURGICAL DEVICE AND RELATED METHOD

BACKGROUND OF THE INVENTION

This invention relates to a laparoscopic surgical device and a related surgical technique.

Laparoscopy involves the piercing of a patient's abdominal wall and the insertion of a cannula through the perforation. Generally, the cannula is a trocar sleeve which surrounds a trocar during an abdomen piercing operation. Upon the formation of the abdominal perforation, the trocar is withdrawn while the sleeve remains traversing the abdominal wall. A laparoscopic instrument, such as a laparoscope or a forceps, is inserted through the cannula so that a distal end of the instrument projects into the abdominal cavity.

Generally, in a laparoscopic surgical procedure, three or four perforations are formed in the abdomen to enable deployment of a sufficient number of laparoscopic instruments to perform the particular surgery being undertaken. Each perforation is formed by a trocar which is surrounded by a sleeve, the sleeves or cannulas all remaining in the abdominal wall during the surgical procedure.

Prior to insertion of the first trocar and its sleeve, a hollow needle called a "Veress needle" is inserted through the abdominal wall to enable pressurization of the abdominal cavity with carbon dioxide. This insufflation procedure distends the abdominal wall, thereby producing a safety space above the patient's abdominal organs.

A problem with this insufflation procedure is that the surgeon has little information for determining the location of the distal end of the Veress needle. Consequently, the carbon dioxide is sometimes injected into the abdominal wall, which results in a subcutaneous emphezema, or into the intestine. The latter eventuality is particularly dangerous in that, subsequently to an inflation of the intestine by carbon dioxide, a trocar is sometimes inserted into the intestine, resulting in a substantial perforation.

OBJECTS OF THE INVENTION

An object of the present invention is to provide an improved method for use in insufflating an abdominal cavity during a laparoscopic procedure.

Another object of the present invention is to provide a method for use in laparoscopic surgery which reduces the incidence of injury to the patient, particularly injury resulting from errors during the insufflation procedure.

A more particular object of the present invention is to provide a method which provides enhanced information to the surgeon about the location of the distal end of the Veress needle relative to internal body organs during an insufflation procedure.

A further object of the present invention is to provide an improved Veress needle assembly for use in such a method.

SUMMARY OF THE INVENTION

A device for use in laparoscopic surgical operations comprises, in accordance with the present invention, a Veress needle assembly including a Veress needle, and a pressure sensor operatively connected to the needle assembly for monitoring pressure. The pressure sensor may be mounted to the needle itself. Alternatively, the pressure sensor may be mounted to an obturator slidably inserted into the needle or to a sleeve slidably surrounding the needle.

According to to another embodiment of the present invention, a device for use in laparoscopic surgical operations comprises a Veress needle assembly including a Veress needle, an ultrasonic wave generator operatively connected to the needle assembly for generating an ultrasonic pressure wave, and an ultrasonic sensor operatively connected to the needle assembly for monitoring ultrasonic pressure waves reflected from internal organs or tissues of the patient located along an insertion path of the needle. The ultrasonic waves are reflected from the organs and tissues upon generation of the waves by the wave generator. An ultrasound analyzer is operatively connected to the sensor for analyzing reflected ultrasonic pressure waves detected by the sensor. An indicator is operatively connected to the analyzer for generating a signal sensible by an operator, the signal indicating objects sensed via the sensor and the analyzer.

Pursuant to another feature of the present invention, the wave generator and the sensor are mounted to the needle, for example, at a distal end thereof. Alternatively, the wave generator and the sensor are mounted to an obturator slidably inserted into the needle or to a sleeve slidably surrounding the needle.

A method for use in performing a laparoscopic surgical operation comprises, in accordance with the present invention, the steps of (i) inserting a Veress needle through an abdominal wall of a patient, (ii) during the step of inserting, automatically monitoring pressure at a distal end of the needle, and (iii) upon detecting a drop in pressure at the distal end of the needle, connecting the needle to a pressure source for inflating an abdominal cavity of the patient. The step of automatically monitoring may be implemented via an obturator slidably inserted into the needle, in which case the method further comprises the step of removing the obturator from the needle prior to the step of connecting the needle to a pressure source. Alternatively, the step of automatically monitoring is implemented via a sleeve about the needle.

A method for use in performing a laparoscopic surgical operation comprises, in accordance with another embodiment of the present invention, the steps of (a) inserting a Veress needle through an abdominal wall of a patient, (b) during the step of inserting, emitting ultrasonic pressure waves in the direction of insertion of the needle, (c) automatically sensing ultrasonic waves reflected from internal tissues in the patient, (d) analyzing the sensed ultrasonic waves to determine internal structures of the patient, (e) upon detecting, via the steps of sensing and analyzing, an abdominal cavity of the patient in the direction of insertion of the needle, manipulating the needle to position a distal end thereof in the detected abdominal cavity, and (f) upon the positioning of the distal end of the needle in the detected abdominal cavity, connecting the needle to a pressure source for inflating the detected abdominal cavity of the patient.

A laparoscopic method in accordance with the present invention for use in insufflating an abdominal cavity during a laparoscopic procedure provides enhanced information to the surgeon about the location of the distal end of the Veress needle relative to internal body organs during an insufflation procedure. Consequently, the likelihood of injury to the patient owing to an improperly positioned Veress needle is reduced, if not eliminated.

DETAILED DESCRIPTION

Figure 1:
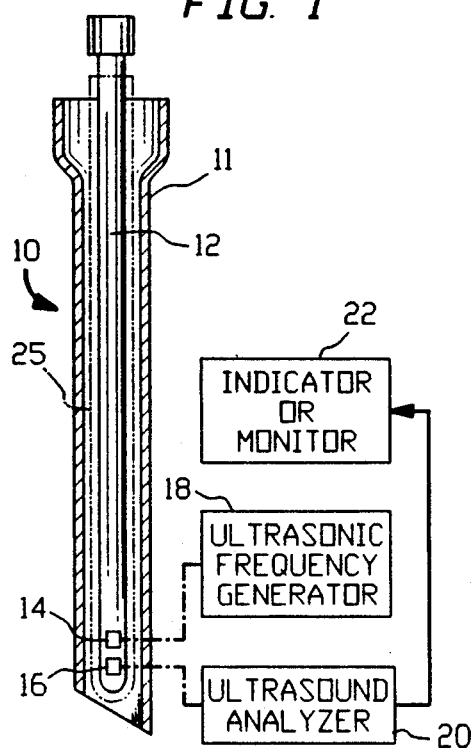
FIG. 1 is a partially a schematic cross-sectional view and partially a block diagram of a device for use in laparoscopic surgery, in accordance with the present invention.

As illustrated in FIG. 1, a device for use in laparoscopic surgical operations comprises a Veress needle assembly 10 including a Veress needle 11 and an obturator 12 slidably inserted provided inside needle 11 Obturator 12 is provided at a distal end with a piezoelectric element 14 and an ultrasonic sensor or transducer 16. Piezoelectric element 14 is operatively connected to an ultrasonic frequency or wave generator 18, while sensor 16 is operatively connected to an ultrasound analyzer 20.

Sensor 26 monitors reflected ultrasonic pressure waves returning to the needle assembly from internal body tissues of a patient upon generation of the waves by frequency generator 18 and piezoelectric element 14. Ultrasound analyzer 20 analyzes the reflected ultrasonic pressure waves detected by sensor 16 to determine the location of internal organic structures of the patient which are located along an insertion path of needle 12.

A monitor or other indicator 22 is operatively connected to analyzer 20 for generating a signal, e.g., a visual image, sensible by an operator, whereby the operator may apprehend the location of internal body organs and tissues disposed distally of needle assembly 10 along the insertion path thereof.

A disposable sheath 25 is removably attached to obturator 12 for protecting the obturator from infectious bacteria and viruses. The sheath is removed and replaced with an identical sheath prior to use of obturator 12 in a subsequent laparoscopic operation.

Figure 2:
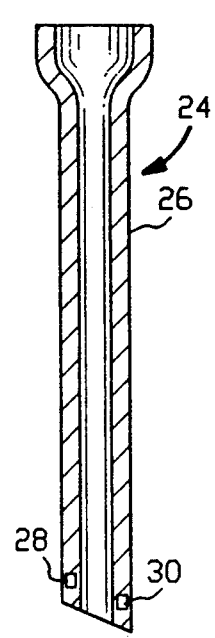
FIG. 2 is a schematic cross-sectional view of another device for use in laparoscopic surgery, in accordance with the present invention.

As depicted in FIG. 2, a Veress needle assembly 24 comprises a Veress needle 26 itself provided at a distal end with a piezoelectric element 28 and an ultrasonic sensor or transducer 30. As discussed above with reference to FIG. 1, piezoelectric element 28 and ultrasonic sensor or transducer 30 are connected to an ultrasonic frequency generator and an ultrasound analyzer (not illustrated in FIG. 2), respectively.

Figure 3:
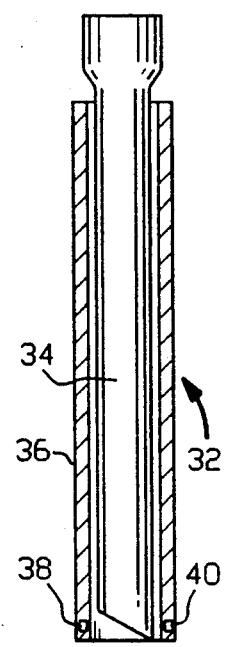
FIG. 3 is a schematic cross-sectional view of a further device for use in laparoscopic surgery, in accordance with the present invention.

As shown in FIG. 3, a Veress needle assembly 32 comprises a Veress needle 34 slidably surrounded by a protective sleeve 36. Sleeve 36 carries at a distal end a piezoelectric element 38 and an ultrasonic sensor or transducer 40. As discussed above with reference to FIG. 1, piezoelectric element 38 and ultrasonic sensor or transducer 40 are connected to an ultrasonic frequency generator and an ultrasound analyzer (not illustrated in FIG. 2), respectively.

In using Veress needle assembly 10, 24 or 32, needle 11, 26 or 34 is used to pierce the abdominal wall of a patient. The assembly 10, 24 or 34 is then inserted slowly through the abdominal wall. During the insertion of needle assembly 10, 24 or 32, ultrasonic frequency generator 18 energizes piezoelectric element 14, 28 or 38 to emit ultrasonic pressure waves in the direction of insertion of needle assembly 10, 24 or 32. Ultrasonic pressure waves which are reflected from internal body organs and tissues of the patient are picked up by sensor 16, 30 or 40 and analyzed by analyzer 20. Internal structures of the patient are then graphically represented on monitor 22. In this way, the surgeon can determine whether the distal end of the needle is located inside the abdominal wall and whether there is a loop of intestine coiled against the abdominal wall in the insertion path of the needle assembly 10, 24 or 32.

Attending to the image on monitor 22, the surgeon manipulates needle assembly 10, 24 or 32 to position a distal end thereof in an abdominal cavity. Upon the positioning of the distal end of needle 11, 26 or 34 in the detected abdominal cavity, the surgeon or an assistant connects needle 11, 24 or 32 to a source of pressurized carbon dioxide (not shown), thereby inflating the detected abdominal cavity of the patient. Of course, in the case of assembly 10, obturator 12 is removed prior to the insufflation or pressurization of the abdominal cavity.

Figure 4:
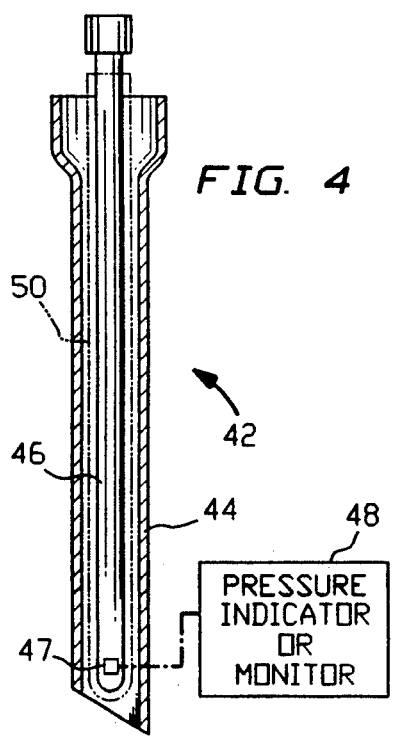
FIG. 4 is a schematic cross-sectional view of yet another device for use in laparoscopic surgery, in accordance with the present invention.

As shown in FIG. 4, another device for use in laparoscopic surgical operations comprises a Veress needle assembly 42 including a Veress needle 44, an obturator 46 slidably inserted in the needle 44, and a pressure sensor 47 mounted to a distal end of obturator 46 for monitoring pressure. Pressure sensor 47 is operatively connected to a gauge or other indicator 48 for providing a visual read-out to an operator, e.g., a surgeon.

A disposable sheath 50 is removably attached to obturator 46 for protecting the obturator from infectious bacteria and viruses. The sheath is removed and replaced with an identical sheath prior to use of obturator 46 in a subsequent laparoscopic operation.

Figure 5:
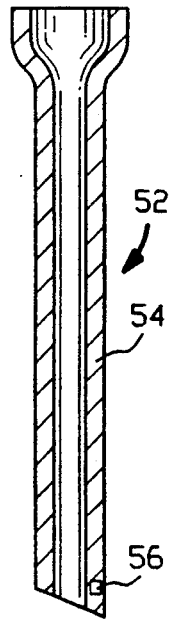
FIG. 5 is a schematic cross-sectional view of an additional device for use in laparoscopic surgery, in accordance with the present invention.

As depicted in FIG. 5, a Veress needle assembly 52 comprises a Veress needle 54 itself provided at a distal end with a pressure sensor or transducer 56. As discussed above with reference to FIG. 4, pressure sensor 56 is connected to a gauge or other indicator 48 (FIG. 4) for providing a visual read-out to an operator, e.g., a surgeon.

Figure 6:
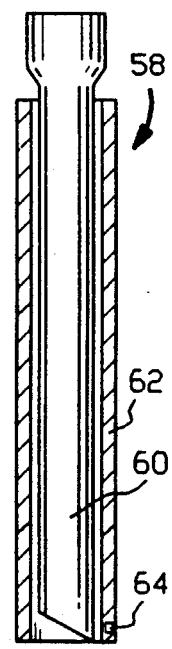
FIG. 6 is a schematic cross-sectional view of yet a further device for use in laparoscopic surgery, in accordance with the present invention.

As illustrated in FIG. 6, a Veress needle assembly 58 comprises a Veress needle 60 slidably surrounded by a protective sleeve 62. Sleeve 62 carries at a distal end a pressure sensor or tranducer 64. As noted above, pressure sensor 56 is connected to a gauge or other indicator 48 (FIG. 4).

In using Veress needle assembly 42, 52 or 58 at the onset of a laparoscopic procedure in order to insufflate a patient's abdomen, needle 44, 54 or 60 is pushed through an abdominal wall of a patient. During the insertion step, pressure sensor 47, 56 or 64 automatically monitors pressure at a distal end of needle 44, 54 or 60. The sensed pressure is displayed on gauge or indicator 48. Upon detecting a drop in pressure at the distal end of needle 44, 53 or 60, the surgeon or an operative assistant connects the needle to a source of pressurized carbon dioxide (not shown) to inflate an abdominal cavity of the patient. Of course, in the case of assembly 42, obturator 46 is removed prior to the insufflation or pressurization of the abdominal cavity.

Although the invention has been described in terms of particular embodiments and applications, one of ordinary skill in the art, in light of this teaching, can generate additional embodiments and modifications without departing from the spirit of or exceeding the scope of the claimed invention. For example, the pressure sensors or ultrasonic transducers may be disposed in different locations other than the illustrated locations. Accordingly, it is to be understood that the drawings and descriptions herein are preferred by way of example to facilitate comprehension of the invention and should not be construed to limit the scope thereof.

What is claimed is:

1. A method for use in performing a laparoscopic surgical operation, comprising the steps of:
   inserting a Veress needle through an abdominal wall of a patient;
   during said step of inserting, automatically monitoring pressure at a distal end of said needle; and
   upon detecting a drop in pressure at said distal end of said needle, connecting said needle to a pressure source for inflating an abdominal cavity of the patient, thereby commencing abdominal insufflation prior to a laparoscopic procedure.

2. The method defined in claim 1 wherein said step of automatically monitoring is implemented via an obturator slidably inserted into said needle, further comprising the step of removing said obturator from said needle prior to said step of connecting said needle to a pressure source.

3. The method defined in claim 1, further comprising the step of inserting said needle into a sleeve prior to said step of inserting, said step of inserting including the step of inserting said sleeve with said needle through said abdominal wall of the patient, said step of automatically monitoring including the step of operating a pressure sensor mounted to said sleeve.

4. A method for use in performing a laparoscopic surgical operation, comprising the steps of:
   inserting a Veress needle through an abdominal wall of a patient;
   during said step of inserting, emitting ultrasonic pressure waves in the direction of insertion of said needle;
   automatically sensing ultrasonic waves reflected from internal tissues in the patient;
   analyzing the sensed ultrasonic waves to determine internal structures of said patient;
   upon detecting, via said steps of sensing and analyzing, an abdominal cavity of said patient in the direction of insertion of said needle, manipulating said needle to position a distal end thereof in the detected abdominal cavity; and
   upon the positioning of the distal end of said needle in the detected abdominal cavity, connecting said needle to a pressure source for inflating the detected abdominal cavity of the patient, thereby commencing abdominal insufflation prior to a laparoscopic procedure.

5. The method defined in claim 4 wherein said steps of emitting and sensing are implemented via an obturator slidably inserted into said needle, further comprising the step of removing said obturator from said needle prior to said step of connecting said needle to a pressure source.

6. The method defined in claim 4, further comprising the step of inserting said needle into a sleeve prior to said step of inserting, said step of inserting including the step of inserting said sleeve with said needle through said abdominal wall of the patient, said steps of emitting and sensing including the respective steps of operating a pressure wave transducer and a pressure sensor mounted to said sleeve.

7. The method defined in claim 4, further comprising the steps of removing said needle from the abdominal wall of the patient in the event that an organ obstruction is detected in the direction of insertion of said needle.

* * * * *